United States Patent
Marmulla

(10) Patent No.: US 6,241,735 B1
(45) Date of Patent: Jun. 5, 2001

(54) SYSTEM AND METHOD FOR BONE SEGMENT NAVIGATION

(76) Inventor: Rüdiger Marmulla, Brunnstrasse 7, D-93053 Regensburg (DE)

(*) Notice: Subject to any disclaimer, the term of this patent is extended or adjusted under 35 U.S.C. 154(b) by 0 days.

(21) Appl. No.: 09/331,931

(22) PCT Filed: Oct. 28, 1998

(86) PCT No.: PCT/EP98/06828

§ 371 Date: Aug. 30, 1999

§ 102(e) Date: Aug. 30, 1999

(87) PCT Pub. No.: WO99/21498

PCT Pub. Date: May 6, 1999

(30) Foreign Application Priority Data

Oct. 28, 1997 (DE) .............................. 197 47 427

(51) Int. Cl.[7] .............................. A61B 17/56; A61B 19/00
(52) U.S. Cl. .............................. 606/102; 606/130
(58) Field of Search .............................. 606/130, 53, 86, 606/102

(56) References Cited

U.S. PATENT DOCUMENTS

| | | |
|---|---|---|
| 5,086,401 | * 2/1992 | Glassman et al. . |
| 5,143,086 | 9/1992 | Duret et al. . |
| 5,249,581 | 10/1993 | Horbal et al. . |
| 5,279,309 | 1/1994 | Taylor et al. . |
| 5,389,101 | * 2/1995 | Heilbrun et al. . |
| 5,880,976 | * 3/1999 | DiGioia, III et al. . |
| 6,006,126 | * 12/1999 | Cosman . |
| 6,074,394 | * 6/2000 | Krause . |

FOREIGN PATENT DOCUMENTS 42 19 939 A1   6/1992   (DE) .............................. A61B/17/58

* cited by examiner

Primary Examiner—Jeffrey A. Smith

(57) ABSTRACT

A system for bone segment navigation with a planning unit for planning a bone segment displacement, a marker arrangement to be connected to a bone segment, a position sensing unit which senses the position of the marker arrangement, and an indication and processing unit, which is connected to the position sensing unit and to the planning unit, in order to indicate the deviation of the present position of the bone segment from a planned final bone segment position or from a planned bone segment displacement path. The marker arrangement is connected in an unambiguously reproducible manner to the bone segment by a template allocated to the bone segment. After the template has been placed and fastened on the bone segment, a correlation is possible between the patient and the image data set or the planning data set, without probing and sensing individual bone points according to position by means of a pointer.

22 Claims, 3 Drawing Sheets

… (1)

SYSTEM AND METHOD FOR BONE SEGMENT NAVIGATION

CROSS-REFERENCES TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The invention relates to a system for bone segment navigation.

2. Discussion of Relevant Art

A system of this kind is known from U.S. Pat. No. 5,279,309 in which the position of the bone segment is sensed by means of markers which are arranged, at a spacing from the bone segment surface, on needles which penetrate into the bone segment surface.

However, this arrangement of the markers, constituted as light emitting diodes (LED), basically leaves open their exact spatial relationship to the bone segment or to a preoperative data set obtained by computerized tomography (CT). This can be obviated by producing the preoperative data set with the needles already inserted into the bone segment, but this of course makes necessary a surgical operation for setting the marker needles which precedes the bone segment displacement proper and which is stressful for the patient, and an additional, so-called planning CT, on which the marker needles are reproduced.

Another possible method of setting the markers in a spatial relationship to the bone segment, as also mentioned in U.S. Pat. No. 5,279,309, consists of sensing both the markers and also the bone segment with the tip of a feeler pin or pointer, the position of which can be measured by means of the position sensing unit. The spatial relationship of the markers relative to the bone segment can be established when, during the operation, unambiguously recognizable points both on the bone segment itself and also in the data set, so-called characteristic points, are touched and sensed according to position. However, the characteristic points then have to be touched and sensed according to position in a time-consuming manner during the operation. Furthermore, this has the precondition that such characteristic points exist.

This is of course not the case in many bone segments, so that the position determination of the bone segment itself as mentioned in U.S. Pat. No. 5,279,309 is not possible with the accuracy required in some cases of application.

SUMMARY OF THE INVENTION

The invention has as its object to provide a system for bone segment navigation, with which the position of any bone segments can be reliably, accurately and rapidly sensed, without having to touch bone points individually and sense them according to position, during the operation.

This object is attained by a system of bone segment navigation comprising:

a planning unit for planning a bone segment displacement, a marker arrangement to be connected to a bone segment, a position sensing unit that senses the position of said marker arrangement, an indication and processing unit connected to said position sensing unit and to said planning unit, in order to indicate a deviation of a present position of said bone segment from a planned bone segment position or from a planned bone segment displacement path, and a template allocated to said bone segment that connects said marker arrangement to said bone segment.

Then by the connection of the marker arrangement with the bone segment by means of a template which is individually associated with the bone segment, there is no longer an assignment to individual characteristic points, but the whole surface of the bone segment can instead be used for an unambiguous allocation of the position of the marker arrangement with the bone segment. After the setting in place and fastening of the template on the bone segment, a correlation is then possible between the patient and an imaging data set or planning data set, without touching and position sensing of individual bone points.

The dependent claims relate to further advantageous embodiments of this invention.

BRIEF DESCRIPTION OF THE DRAWINGS

The invention will be described hereinbelow by means of an embodiment example and with reference to the accompanying drawings.

DETAILED DESCRIPTION OF PREFERRED EMBODIMENTS

Figure 1:
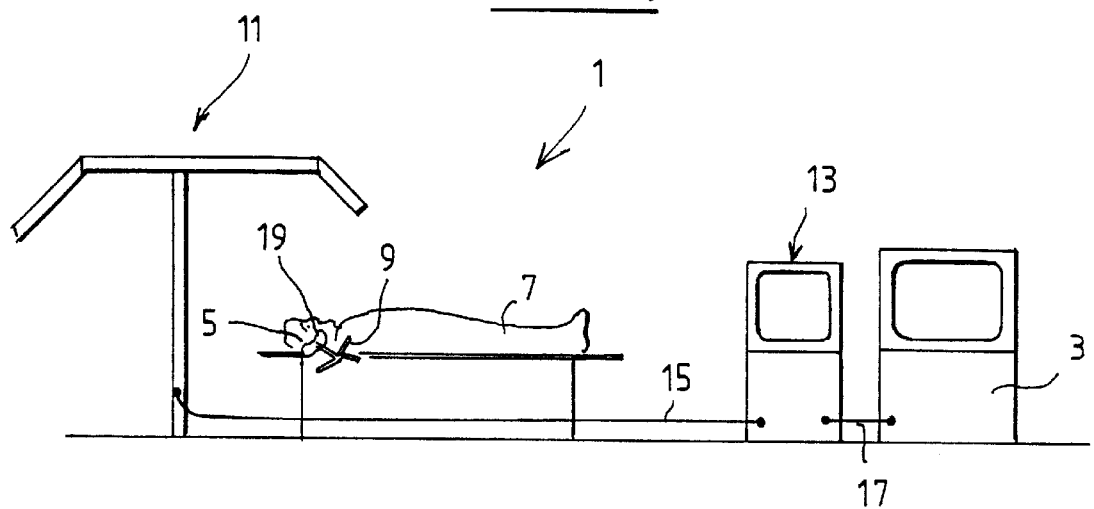
FIG. 1 shows a schematic illustration of a system for bone segment navigation according to the invention.

A system 1 according to the invention for bone segment navigation is shown in FIG. 1. The system 1 includes a planning unit 3 which preferably has a display screen and which makes possible the planning of a bone segment displacement by means of a preoperative data set produced, e.g., by CT.

A bone segment 5 of a patient 7 is to be displaced in a pre-planned manner relative to the rest of the patient 7, especially relative to his facial skeleton.

A marker arrangement 9 is attached by means of a template 19 to the bone segment 5 to be displaced, and its position can be measured by a position sensing unit 11. The individual markers of the marker arrangement 9 are infrared light emitting diodes, the position of which can be sensed by the position sensing unit 11, which includes three infrared sensitive cameras. However, the individual markers can also be passive reflectors, or ultrasonic transmitters.

The sensed marker positions are input via a signal lead 15 to an indication and processing unit 13, which is further connected, via a further signal lead 17, to the planning unit 3. The planned displacement path or the planned final position or final orientation of the bone segment 5 is thereby also input to the indication and processing unit 13.

The indication and processing unit 13 calculates the deviation of the actual position of the bone segment 5 from its planned final position, and indicates this deviation to the surgeon, graphically and/or by means of coordinates.

The surface of the bone segment to be navigated, that is, to be displaced in a defined manner, can be reproduced by the planning unit 3 and/or by the indication and processing unit 13 as a polygonal or abstracted triangular structure which within the operation is to be brought into coincidence with a congruent figure in the final or target position.

A computer-controlled mechanical arm of a robot can also be arranged on the system, and automatically guide the bone segment according to the initial and target coordinates into the desired position and hold it fixed there.

Figure 2:
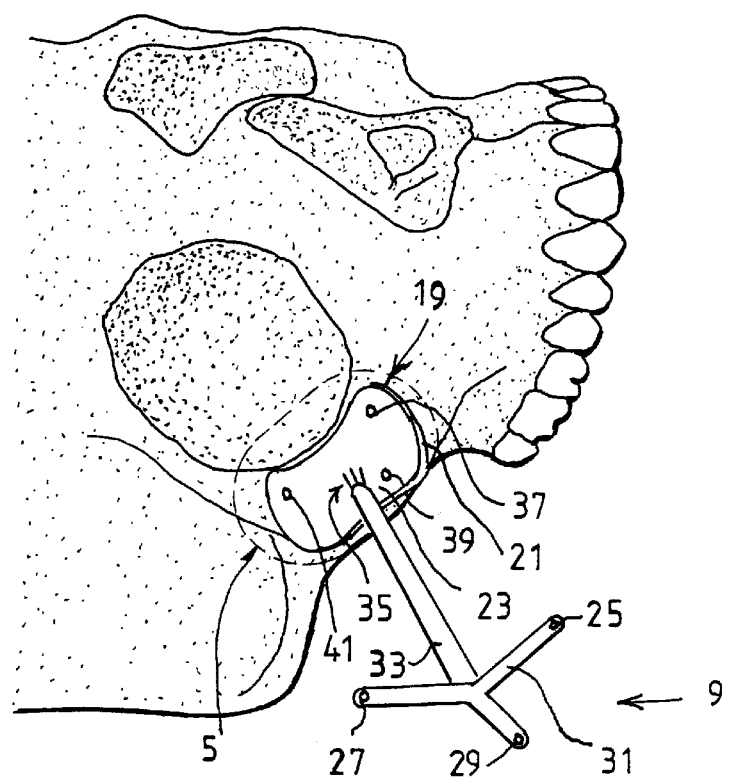
FIG. 2 shows a schematic illustration of the template of FIG. 1, in detail.

FIG. 2 shows the template 19 which is specifically associated with the bone segment 5 indicated by a dashed edge line, and is connected by means of osteosynthesis screws or with ligatures, not shown in FIG. 2, to the bone segment 5. The template 19 has a mating surface portion 23 with a mating surface 21 which is adapted to the shape of the respective convex and concave surface regions of the bone segment 5 and which insures unambiguous allocation of the marker arrangement 9 to the bone segment 5. It should be noted that the mating surface 21 in FIG. 2 is arranged on the back side, which cannot be seen, of the mating surface portion 23.

The unambiguously reproducible allocation between the bone segment and the markers arranged in the template is thus insured by a lock-and-key principle.

Since the template 19 can already be produced by reference to the preoperative data set, a surgical operation, preceding the bone segment operation proper, for the placement of markers which then appear in the preoperative data set is thus superfluous. The production of a 3D-model for the manufacture of the template is thereby restricted, in a manner which reduces costs, to the surface of the bone segment to be navigated.

The marker arrangement 9 includes infrared light emitting diodes 25, 27, 29, which are fitted to the outer ends of a three-spoked carrier structure 31. The carrier structure 31 is releasably connected to the surface portion 23 of the template 19 by means of an elongate handle portion 33. The handle portion 33 is connected thereto by means of an unambiguously reproducible plug type connection to the mating surface portion 23. The connection consists of three pins 35 which form a male die and which cooperate with a female die which can be polymerized into the mating surface portion 23.

Windows 37, 39 and 41 in the mating surface portion 23 are denoted by 37, 39 and 41; by means of them, a pointer tip could directly contact the surface of the bone segment 5, in order to directly measure the position of selected regions of the surface of the bone segment 5. However, since the use of a pointer during the operation is time-consuming, the windows 37, 39 and 41 are principally of advantage with a view to operation planning on a model bone segment.

A bone segment navigation with the system according to the invention can take its course as follows:

1. Determination of the initial or actual position of bone reference points with the planning unit, by means of a preoperative three-dimensional data set. According to the invention, the bone reference points do not have to be characteristic points, since they can be unambiguously determined by means of the specific template mating surface.
2. Determination of the final or desired position of the bone reference points with the planning unit.
3. Manufacture of the template, by means of the preoperative three-dimensional data set.
4. Determination of the marker positions on the individual template relative to the bone reference points.
5. Calculation of the planned end positions of the marker arrangement by means of the actual and desired positions of the bone reference points.
6. At the beginning of the operation proper, the placement of the template on the bone segment of the patient and fastening of the template with osteosynthesis screws or wire ligatures.
7. Determination of the marker positions on the patient before osteotomy.
8. Calculation of the actual positions of the bone reference points on the patient.
9. Calculation of the desired positions of the marker arrangement by means of the preoperative planning.
10. Calculation of the desired positions of the bone reference points on the patient by means of the preoperative planning.
11. Sensing of the movement or of the positions of the marker arrangement with the position sensing unit.
12. Determination of the actual position of the bone reference points.
13. Calculation of the distance between the present position, actual position and desired position of the marker arrangement.
14. Calculation of the distance between present position, actual position and desired position of the bone reference points.

It should be noted that steps 1–5 take place in the laboratory, before the surgical operation proper, and that during the surgical operation on the patient, no individual bone points have to be probed with a pointer and sensed as regards position.

Figure 3A:
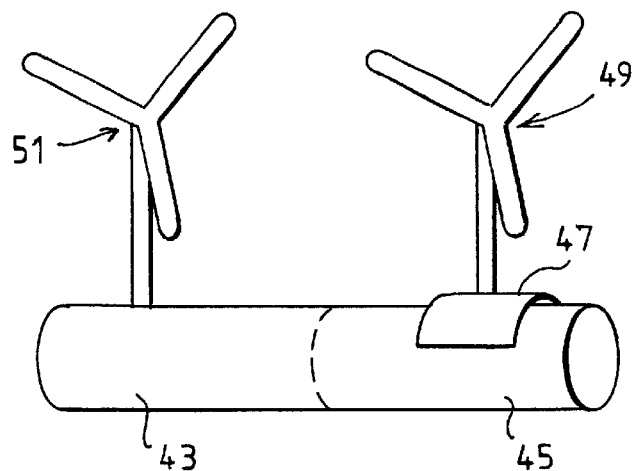
FIGS. 3a–3f show a schematic illustration of the course of a bone segment navigation with a system according to the invention.
Figure 3B:
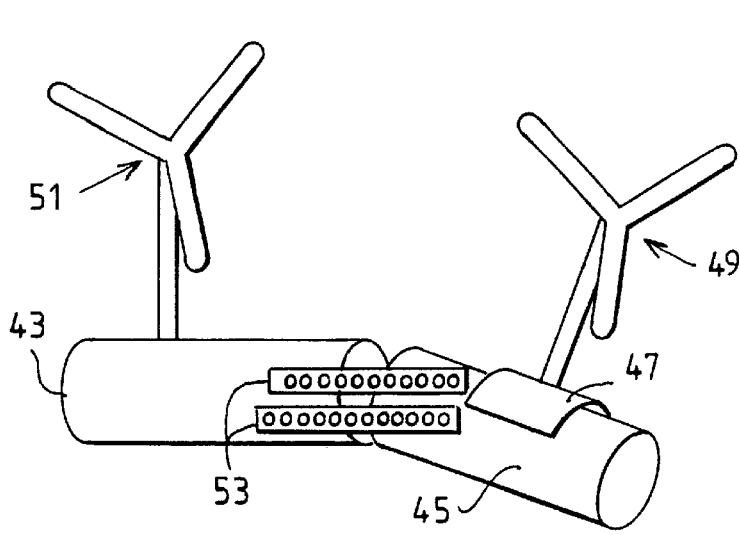
Figure 3C:
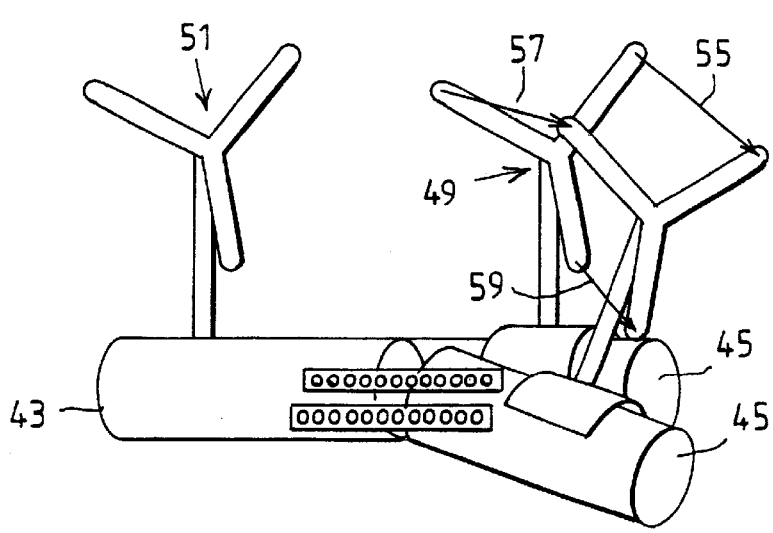

The course of a bone segment navigation with the system according to the invention is shown schematically in FIGS. 3a–3f; FIGS. 3a–3c relate to operation planning, and FIGS. 3d–3f relate to the operation proper.

In FIG. 3a, a stereolithographically produced three-dimensional model 43 of a bone structure to be treated surgically, for example a skull, is shown very schematically. The model bone structure 43 has a region 45 which corresponds as a model bone segment to the bone segment of the skull to be navigated.

In the planning of the operation, the surgical intervention by a suitable displacement of the model bone segment 45 relative to the model bone structure 43 is played through, and the data obtained thereby are input into the planning unit 3.

A template 47 produced by means of preoperative diagnostic data, e.g. CT-scans, fits exactly and reproducibly as to location to the model bone segment 45. A marker arrangement 49 which corresponds to the marker arrangement 9 of FIG. 2 is arranged, fixed in position and orientation, on this template 47. Furthermore, a further marker arrangement 51 is rigidly connected to the model bone structure 43, so that fixation of the model bone structure 43 relative to the position sensing unit 11 during the operation planning symbolically represented in FIGS. 3a–3c can be dispensed with.

FIG. 3a corresponds to the initial or actual position of the bone segment before its displacement. This initial position is sensed with the position sensing unit 11 shown in FIG. 1 by measurement of the position and orientation of the marker arrangement 49 relative to the marker arrangement 51, and is input to the planning unit 3.

On the model, an osteotomy separating the bone segment from the bone structure is then simulated or carried out on the model, whereby the model bone segment 45 is separated from the model bone structure 43. Next, the model bone segment 45 is then brought into the desired final or desired position, and is fixed, for example with osteosynthesis plates 53, in the final position shown in FIG. 3b. The position sensing unit 11 thereby senses the position and orientation of the marker arrangement 49 relative to the marker arrangement 51 in the final position and, if necessary, additionally in intermediate positions on the planned path between the initial and final positions.

The planning unit 3 calculates, from the initial position of the marker arrangement 49 and the final position of the marker arrangement 49, the vectors 55, 57 and 59 shown in FIG. 3c, which then make possible the determination of the planned final position of the bone segment starting from the initial position of the bone segment, in the surgical operation proper.

FIG. 3c shows the model bone segment 45 and the marker arrangement in a superposed illustration, in both their initial position and also their final position.

Figure 3D:
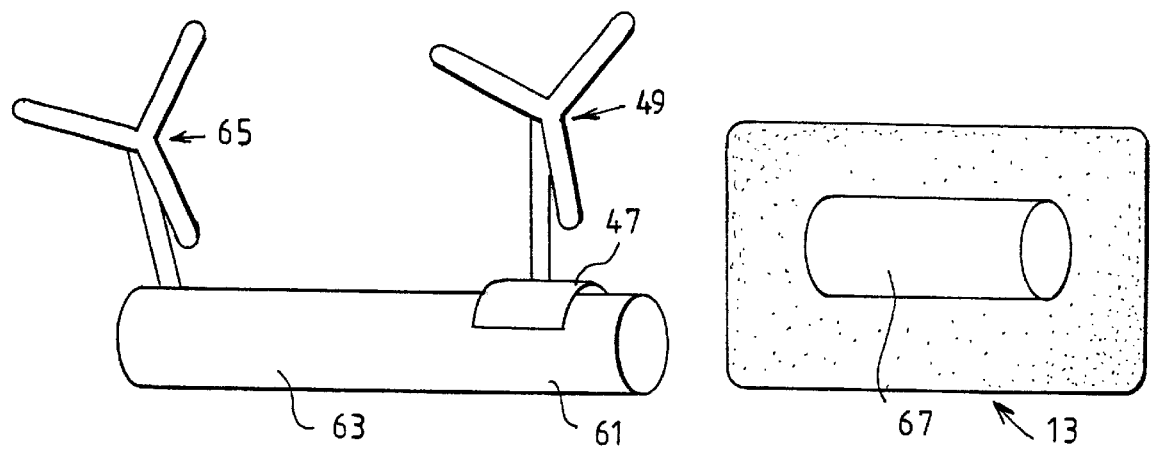
Figure 3E:
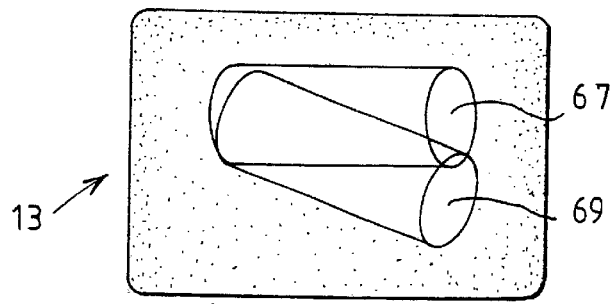
Figure 3F:
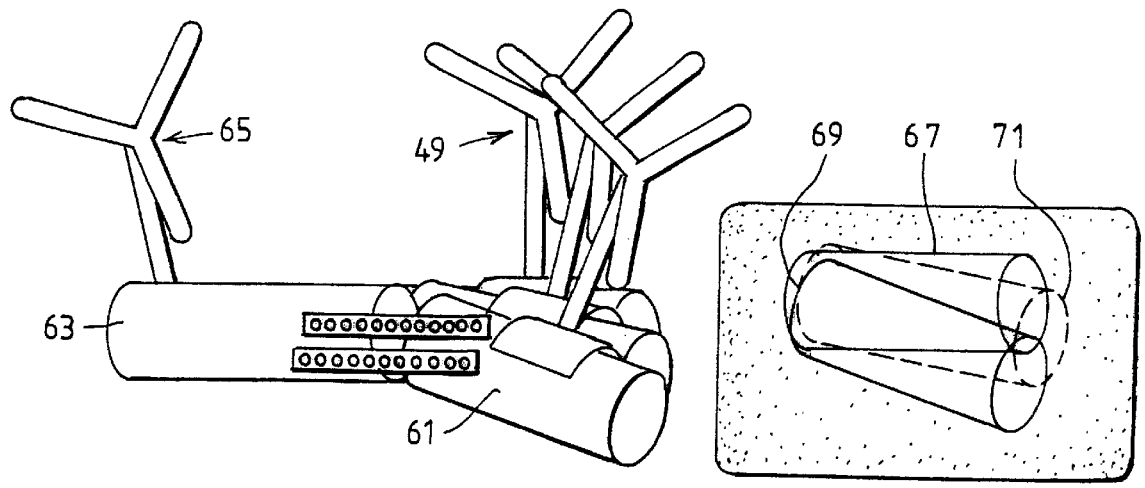

In FIGS. 3d-3f, the operation proper which is carried out on the patient is shown symbolically.

The bone structure 63 on which the model bone structure 43 is based, and the bone segment 61 on which the model bone segment 45 is based, can be recognized in FIG. 3d.

In a first operation section shown in FIG. 3d, the template 47 together with the marker arrangement 49 is arranged, by means of its mating surface, in an unambiguous positional and orientation relationship on the bone segment 61. A marker arrangement 65 is furthermore fastened in a rigid manner to the bone structure 63; in this, care does not have to be taken that the marker arrangement 65 and bone structure 63 reproduce the positional and orientation relationship of the marker arrangement 51 and model bone structure 43 (FIGS. 3a–3c).

The position of the marker arrangement 49 (relative to the marker arrangement 65) is then sensed by means of the position sensing unit 11. Since the unit of template 47 and marker arrangement 49 which was used during operation planning is used unchanged in the operation, the indication and processing unit 13 can calculate from them the initial position of the bone segment 61 and represent it as a set of outlines 67.

In a next operation step shown in FIG. 3e, the indication and processing unit 13 calculates the previously planned final position of the bone segment 61, by means of the vectors 55, 57 and 59 and the position and orientation of the marker arrangement 49 previously sensed in the initial position of the bone segment 61, and represents it as a set of outlines 69.

The surgical operation which includes the osteotomy, bone segment displacement, and osteosynthesis is then proceeded with, and during it the position of the bone segment 61 at any given time is continuously sensed by means of the marker arrangements 49 and 65 and the position sensing unit 11, and is successively represented by the indication and processing unit 13.

An intermediate position of the bone segment 61, besides the initial and final positions of the bone segment 61, is shown in FIG. 3f. This intermediate position can be seen as an outline 71 together with the initial position illustration 67 and the final position illustration 69.

Thanks to the marker arrangement 65, the patient does not have to be fixed absolutely rigidly and immovably relative to the position sensing unit 11 during the operation. However, by fixing the patient, or the bone structure 63, the marker arrangement 65 can be dispensed with.

The three-dimensional model of the bone structure and bone segment does not only serve, in the operation planning according to FIGS. 3a–3c, for the physical simulation of the operation proper, but also so that the position and orientation of the marker arrangement 49 relative to the template 47 do not have to be sensed separately. The orientation in which the marker arrangement 49 is fitted to the template is thus completely indifferent—it only matters that the same, unchanged unit of marker arrangement 49 and template 47 is used in both the operation planning and the operation. In this manner, inadvertent inaccuracies in the connection of the marker arrangement 49 to the template 47 do not have disadvantageous effects on the accuracy of the bone segment navigation.

When, however, the position and orientation of the marker arrangement 49 relative to the template 47 can be sensed with sufficient accuracy, for example by probing the mating surface of the template 47 with a pointer, the three-dimensional model of the bone structure and bone segment can be dispensed with, and the operation can be planned in advance virtually on the planning unit 3.

The template 47 is then individually manufactured as a negative mold directly from the patient data set, and is then connected to the marker arrangement 49. Thereafter the position and orientation of the marker arrangement 49 relative to the mating surface of the template 47 is determined and is input to, or projected into, the patient data set. Thereupon the bone segment displacement with the accompanying position change of the marker can be simulated virtually on the planning unit 3.

What is claimed is:

1. A system for bone segment navigation, comprising:
   a planning unit,
   a marker arrangement,
   a position sensing unit that senses the position of said marker arrangement,
   an indication and processing unit connected to said position sensing unit and to said planning unit in order to indicate a deviation of a present position of said marker arrangement from a planned marker arrangement position or from a planned marker arrangement displacement path, and
   a template allocated to a bone segment to be navigated,
   wherein said marker arrangement is connected to said template, and
   wherein said template comprises a mating surface that fits close and two dimensionally and in an unambiguously reproducible manner against said bone segment to be navigated.

2. The system for bone navigation according to claim 1, wherein said marker arrangement is releasably attached to said template.

3. The system for bone navigation according to claim 2, in which said marker arrangement includes at least three markers fitted directly to said template.

4. The system for bone navigation according to claim 1, wherein said marker arrangement is releasably fitted to said template.

5. The system for bone navigation according to claim 1, further comprising osteosynthesis screws that connect said template fast to said bone segment.

6. The system for bone navigation according to claim 1, further comprising an elongate handle portion connected to said template at one end and to said marker arrangement at another end.

7. The system for bone navigation according to claim 6, in which said marker arrangement includes at least three markers arranged on a carrier structure extending transversely of said elongate handle portion.

8. The system for bone navigation according to claim 7, in which said markers comprise infrared transmitters.

9. The system for bone navigation according to claim 7, wherein said indication and processing unit indicates a deviation of a present position of said marker arrangement from a planned final position of said marker arrangement as abstract triangular or polygonal surface structures that can be brought into coincidence with congruent figures in a target position.

10. The system for bone navigation according to claim 6, in which said marker arrangement includes at least three markers fitted directly to said template.

11. The system for bone navigation according to claim 6, wherein said mating surface of said template has windows to determine the position of points of a bone segment surface directly by a pointer.

12. The system for bone navigation according to claim 6, wherein said indication and processing unit indicates a deviation of a present position of said marker arrangement from a planned final position of said marker arrangement as abstract triangular or polygonal surface structures that can be brought into coincidence with congruent figures in a target position.

13. The system for bone navigation according to claim 1, in which said marker arrangement includes at least three markers attaches directly to said template.

14. The system for bone navigation according to claim 13, wherein said indication and processing unit indicates a deviation of a present position of said marker arrangement from a planned final position of said marker arrangement as abstract triangular or polygonal surface structures that can be brought into coincidence with congruent figures in a target position.

15. The system for bone navigation according to claim 1, in which said marker arrangement includes at least three markers fitted directly to said template.

16. The system for bone navigation according to claim 1, in which said marker arrangement comprises infrared transmitters.

17. The system for bone navigation according to claim 1, wherein said indication and processing unit indicates the deviation of a present position of said marker arrangement from a planned final position of said marker arrangement via coordinates.

18. The system for bone navigation according to claim 1, wherein said indication and processing unit indicates a deviation of a present position of said marker arrangement from a planned final position of said marker arrangement as abstract triangular or polygonal surface structures that can be brought into coincidence with congruent figures in said final position.

19. The system for bone navigation according to claim 1, further comprising an arm of a robot controlled by said indicator and processing unit, that displaces said bone segment.

20. A method for bone segment navigation with a navigation system comprising a planning unit, a marker arrangement, a position sensing unit that senses the position of said marker arrangement and an indication and processing unit connected to said position sensing unit and to said planning unit in order to indicate a deviation of a present position of said bone segment from a planned bone segment position or from a planned bone segment displacement path, comprising the steps of:
    providing a template allocated to said bone segment to be navigated, said template comprising a mating surface that fits close and two dimensionally and in an unambiguously reproducible manner against said bone segment to be navigated to which template said marker arrangement is connected,
    connecting said template to said bone segment to be navigated by means of said mating surface,
    sensing the position of said marker arrangement by said position sensing unit, and navigating said bone segment to be navigated on the basis of said position data of said marker arrangement sensed by said position sensing unit.

21. The method according to claim 20, said method further comprising the steps of:
    recording a pre-operative three-dimensional data set of said bone segment to be navigated,
    selecting reference points with said planning unit by means of said three-dimensional data set,
    determining initial and final positions of said reference points with said planning unit,
    forming said template by means of said pre-operative three dimensional data set, connecting said marker arrangement to said template,
    determining a position of said marker on said template relative to said bone reference points, and
    calculating planned end-positions of said marker arrangement by means of actual and desired positions of said hone reference points and on the basis of said determined position of said marker relative to said bone reference points.

22. A method for bone segment navigation with a navigation system comprising a
    planning unit for planning a bone segment displacement, a marker arrangement, a position sensing unit that senses the position of said marker arrangement, and an indication and processing unit connected to said position sensing unit and to said planning unit in order to indicate a deviation of a present position of a bone segment from a planned bone segment position or from a planned bone segment displacement path, comprising the steps of:
    recording a pre-operative three dimensional data set of said bone segment,
    selecting reference points with said planning unit by means of said three-dimensional data set,
    determining initial and final positions of said reference points with said planning unit,
    providing a model bone structure comprising a portion corresponding to said bone segment to be navigated on the basis of said pre-dimensional date set,
    providing a template by means of said three dimensional data set, wherein said template comprises a mating surface that fits close and two dimensionally and in an unambiguously reproducible manner against said portion of said model bone structure corresponding to said bone segment to be navigated,
    connecting said marker arrangement to said template,
    determining an actual position of said marker arrangement relative to said bone reference points,
    connecting a further marker arrangement to another portion of said model bone structure,
    simulating said bone segment navigation with said model bone structure in order to bring said portion corresponding to said bone segment to be navigated into its desired final position with position and orientation data of said marker arrangement being sensed by said position sensing unit,
    calculating from the initial position of said marker arrangement and said desired final position of said marker arrangement vectors indicating said planned desired final position of said bone segment starting from said initial position of said bone segment,
    connecting said template to said bone segment to be navigated and sensing position data of said marker arrangement by said position sensing unit, and
    navigating said bone segment from its initial position to said desired final position while said indication and processing unit indicates a deviation of an actual position of said bone segment from said desired final position of said bone segment or from a planned bone segment displacement path on the basis of the data recorded during said simulation step.

* * * * *